United States Patent [19]
Hishida

[11] Patent Number: 5,220,925
[45] Date of Patent: Jun. 22, 1993

[54] ELECTRONIC SPHYGMOMANOMETER

[75] Inventor: Hiroshi Hishida, Saitama, Japan

[73] Assignee: Citizen Watch Co., Ltd., Tokyo, Japan

[21] Appl. No.: 724,047

[22] Filed: Jul. 1, 1991

[30] Foreign Application Priority Data

Jul. 3, 1990 [JP] Japan .................. 2-70954[U]

[51] Int. Cl.⁵ .............................................. A61B 5/02
[52] U.S. Cl. ................................... 128/680; 128/685; 128/681
[58] Field of Search ................. 251/4, 8; 128/677–686

[56] References Cited

U.S. PATENT DOCUMENTS

| | | | |
|---|---|---|---|
| 3,624,800 | 11/1971 | Swick | 251/4 |
| 4,200,259 | 4/1980 | Ueda | 128/685 |
| 4,497,323 | 2/1985 | Matsuura et al. | 128/685 |
| 5,031,631 | 7/1991 | Kawamura et al. | 128/685 |

FOREIGN PATENT DOCUMENTS

| | | | |
|---|---|---|---|
| 0269907 | 3/1913 | Fed. Rep. of Germany | 251/4 |
| 0316572 | 12/1989 | Japan | 251/4 |

*Primary Examiner*—Kyle L. Howell
*Assistant Examiner*—Robert L. Nasser, Jr.
*Attorney, Agent, or Firm*—Townsend and Townsend Khourie and Crew

[57] ABSTRACT

A sphygmomanometer including a constant rate air-bleed valve for that is coupled to a cuff for reducing the pressure in the cuff. The valve has a valve casing and a tubular member in the casing. A slit in the tubular member allows air to bleed from the cuff at the constant rate and a regulator is provided for adjusting the bleed rate.

7 Claims, 4 Drawing Sheets

PRIOR ART

ELECTRONIC SPHYGMOMANOMETER

BACKGROUND OF THE INVENTION

1. Field of the Invention

The present invention relates to an electronic sphygmomanometer, and, in particular, to a constant rate air-bleed adjustment device for a sphygmomanometer whereby the pressure in a cuff can be easily adjusted to drop at a substantially uniform rate.

2. Description of the Prior Art

Conventional electronic sphygmomanometers wherein a cuff is pressurized by means of a battery-driven electric pump, a pulse and the air pressure inside the cuff are detected by a pressure sensor, and the systolic and diastolic blood pressure values of a patient whose blood pressure is being measured are obtained and displayed on a digital display device are in widespread use.

In this type of electronic sphygmomanometer, a constant rate air-bleed device is used in order to reduce the pressure of the air inside the cuff at a constant rate.

FIG. 1 shows one example of a constant rate air-bleed valve used with a conventional electronic sphygmomanometer.

In this constant rate air-bleed valve, a flange section 2a of a tubular member 2, as shown in FIG. 2, is insertedly pressed into an inner section of an air-bleed valve casing 1 with a pressure side part 1a by means of a nut 3, and, in addition, a regulating member 4 is screwed into the nut 3 (as, for example, in Japanese Patent Publication 63-14809).

The flange section 2a is provided on one end of the tubular member 2, as shown in FIG. 2, and on the outer peripheral side surface of the tubular member 2, a slit 2b is provided, extending in the longitudinal direction from the flange section 2a. An air-bleed hole 4a is formed in the center of the regulating member 4, and an end 4b of the regulating member 4 contacts the flange section 2a of the tubular member 2. The rate of pressure reduction is regulated by screwing in the regulating member 4, thus increasing the pressure on the the tubular member 2 in the thrust direction, so that the amount of open area of the longitudinal slit 2b increases, corresponding to this pressure.

Accordingly, in this type of conventional constant-rate air-bleed valve, because the longitudinal slit 2a is provided in the tubular member 2, a uniform length in the longitudinal direction is absolutely necessary to obtain good characteristics. In addition, because pressure must be added in the thrust direction, the length of the regulating section in the longitudinal direction must be great. Also, to ensure that the regulating section is airtight, the regulating section must also be large in the radial direction. This gives rise to the drawback that the overall air-bleed valve must be large.

SUMMARY OF THE INVENTION

An object of the present invention is to provide, with due consideration to the drawbacks of such conventional devices, a small-sized, high-performance electronic sphygmomanometer wherein the rate of drop of the air pressure can be easily adjusted as a result of improvements to the air bleed valve so that blood pressure can be precisely measured with a minimum of error.

The object of the present invention is achieved by the provision of an electronic sphygmomanometer with a configuration wherein, in the air piping system, an open end of a tubular member, which is the main body of an air-bleed valve, is positioned on the low pressure side; the other end, which is a closed end, is positioned on the high pressure side, specifically, the airflow intake end during air bleed; and this other end is provided with a radial slit at the closed end of the tubular member which is formed from an elastic member; and the slit is caused to open by an adjustment member which applies pressure to the cylindrical surface of the tubular member.

In this configuration, when the pressure in the cuff is high during the measurement of the blood pressure, the slit opening in the tubular member remains narrow because of the backpressure applied by the adjustment member. When the pressure in the cuff drops, the opening widens in proportion to this drop because the cylindrical member returns to its original shape. Specifically, it is possible to maintain a constant rate of pressure drop by a minute change in the area of the opening in the slit. In addition, the shape of the tubular member and its hardness and elasticity are determined during the design process so that the rate of pressure drop can be controlled by setting the amount of opening in the slit with the adjustment member.

BRIEF DESCRIPTION OF ACCOMPANYING DRAWINGS

These and other objects, features, and advantages of the present invention will become more apparent from the following description of the preferred embodiments taken in conjunction with the accompanying drawings, in which.

DETAILED DESCRIPTION OF THE PREFERRED EMBODIMENTS

The present invention will now be explained with reference to the drawings.

Figure 1:
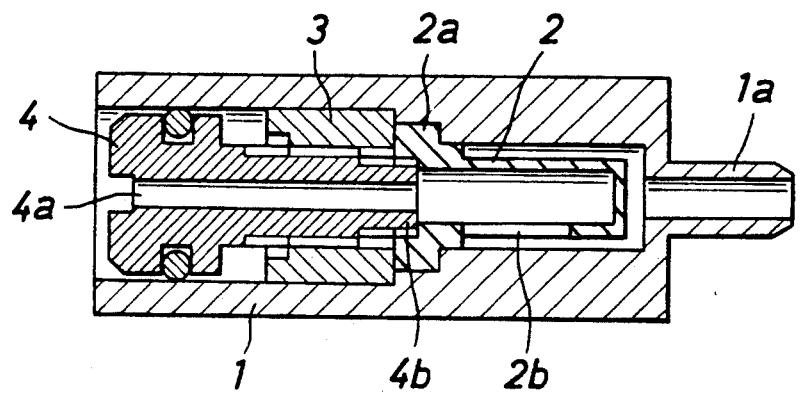
FIG. 1 is a sectional view of a constant rate air-bleed valve used with a conventional electronic sphygmomanometer.
Figure 2:
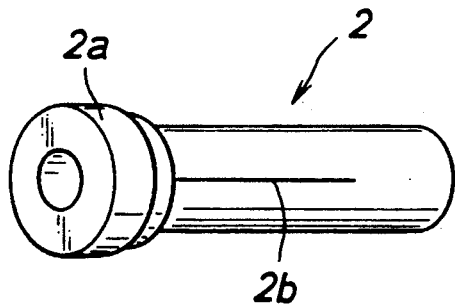
FIG. 2 is a perspective view of a tubular member incorporating the constant rate airbleed valve shown in FIG. 1.
Figure 3:
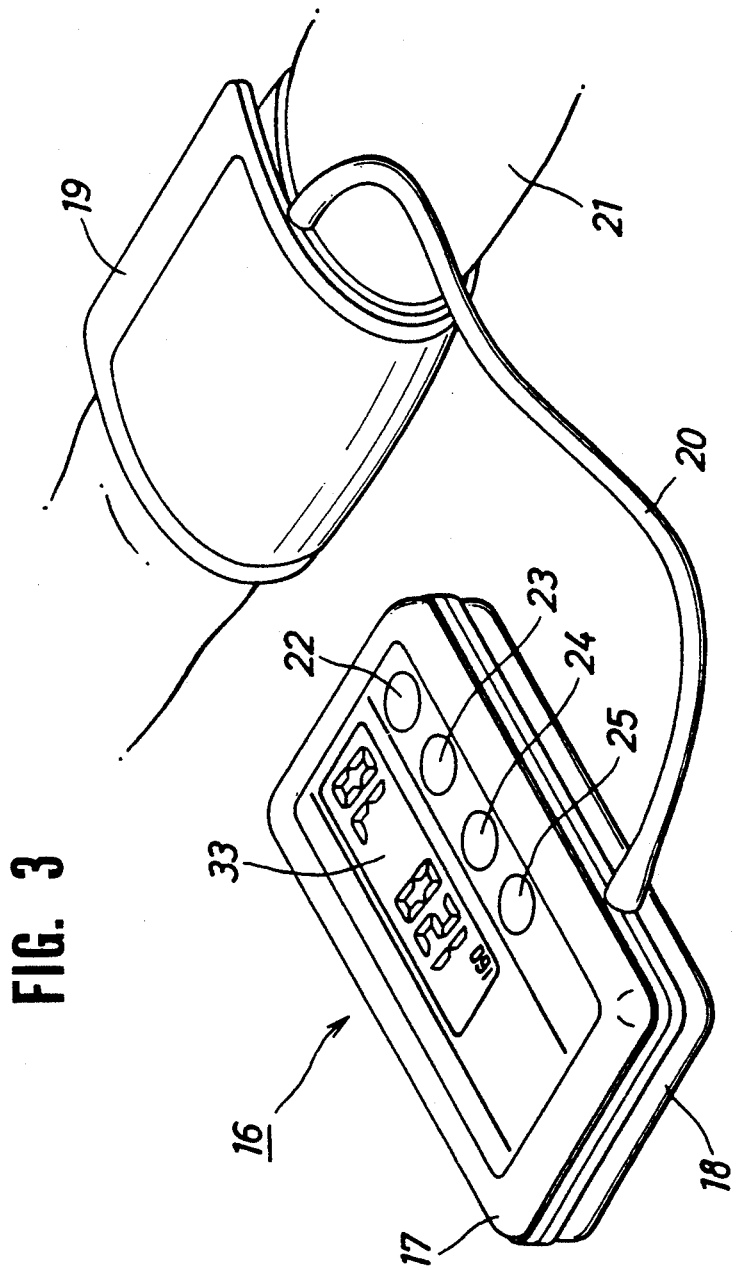
FIG. 3 is a perspective view showing the conditions of use of the electronic sphygmomanometer of the present invention.

FIG. 3 shows the conditions of use of the electronic sphygmomanometer of the present invention.

An electronic sphygmomanometer 16 comprises a main body, made up of an upper casing 17 and a lower casing 18, and a cuff 19 to be applied to an arm 21, the main body and the cuff 19 being joined through a rubber tube 20. A liquid crystal display device 33 for displaying the blood pressure of patient being examined and the initially set pressurization value is provided on the surface of the upper casing 17 together with a power switch 22, a measurement switch 23 for starting the measurement, a memory switch 24 for storing the measured blood pressure values in memory, and an initial pressurization value set switch 25 for optionally setting the initial pressurization value at the cuff.

Figure 4:
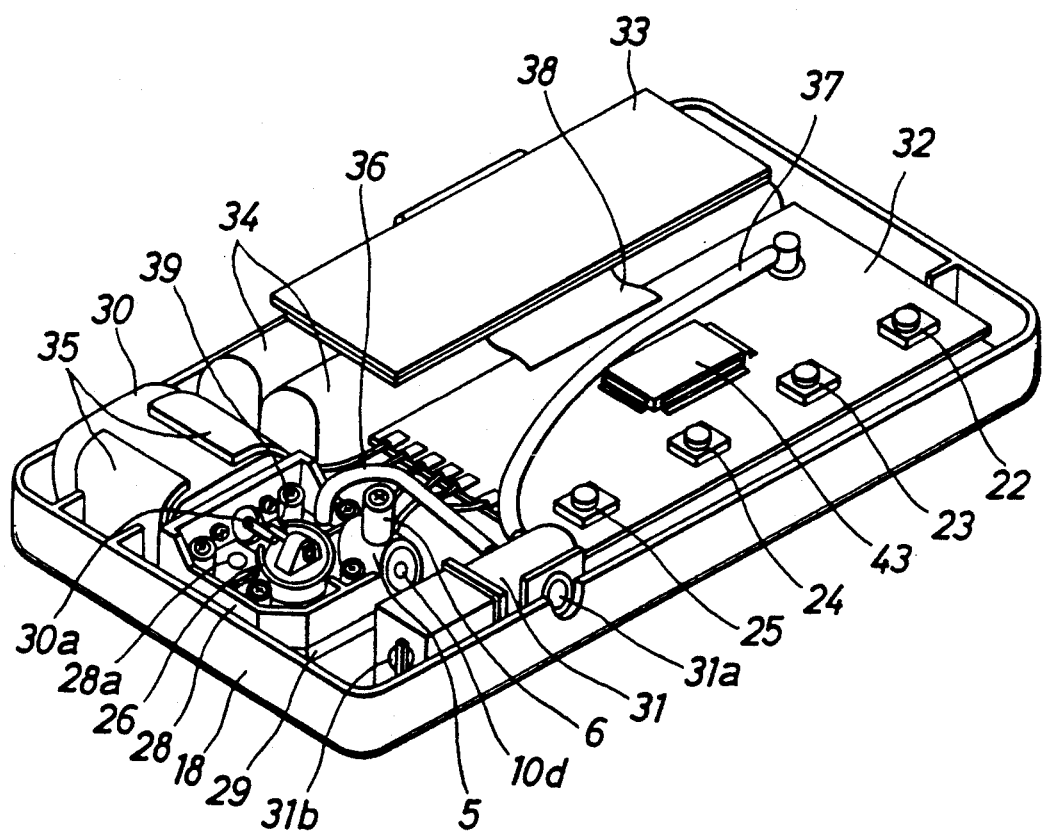
FIG. 4 is a perspective view showing the electronic sphygmomanometer of the present invention with the upper casing removed.

Next, the internal configuration of the electronic sphygmomanometer 16 will be explained based on FIG. 4. FIG. 4 shows the state of the electronic sphygmomanometer 16 with the upper casing 17 and the rubber tube 20 removed. The main components of the internal section of the electronic sphygmomanometer 16 are a pressure pump 2b, a magnetic valve 31, a circuit substrate 32, the liquid crystal display device 33, and a battery housing chamber 34.

Figure 5:
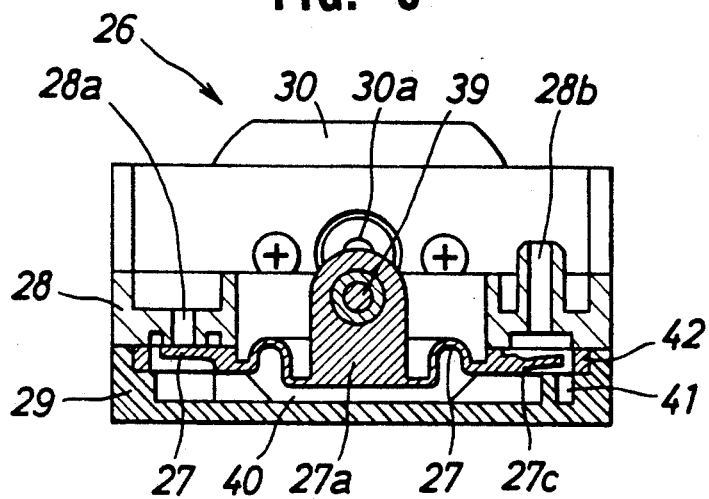
FIG. 5 is an end elevation of a pressure pump for the electronic sphygmomanometer of the present invention.

The pressure pump 26 as shown in FIG. 5 is a diaphragm compressor which is provided with a diaphragm 27 fabricated from nitrile butadiene rubber (hereinafter NBR). The center section of the diaphragm 27 has a mounting section 27a provided with a shaft 39. In addition, an air intake valve 27b and an air-bleed valve 27c are provided on the outer peripheral section of the diaphragm 27, and the inner peripheral sections of the air intake valve 27b and the air-bleed valve 27c are interposedly secured between an upper pump casing 28 and a lower pump casing 29.

The upper pump casing 28 is provided with an air intake port 28a and an air-bleed port 28b respectively positioned opposite the air intake valve 27b and the air-bleed valve 27c of the diaphragm 27. The upper pump casing 28 is integrally formed with a later-described air-bleed valve casing 5. A chamber 40 is formed between the diaphragm 27 and the lower pump casing 29, and a packing 42 is provided to hermetically seal the upper pump casing 28 and the lower pump casing 29.

A motor 30 is provided to activate the diaphragm 27 in the vertical direction. The shaft 39 provided on the mounting section 27a of the diaphragm 27 is eccentrically mounted on a shaft 30a of the motor 30.

A channel 41 communicates with the air-bleed port 28b and is connected to a pressure side port of a later-described constant rate air bleed valve 27c for the sphygmomanometer.

A rubber tube 36 is provided for introducing the air exiting from the air-bleed port 28b to a pressurizing port 31a of the magnetic valve 31. The rubber tube 20 is connected to the pressurizing port 31a of the magnetic valve 31, and feeds the air into the cuff 19. One end of a rubber tube 37 is connected to the magnetic valve 31 and communicates with the pressurizing port 31a. The other end of the rubber tube 37 is connected to a pressure sensor (omitted from the drawings) mounted on the circuit board 32. The magnetic valve 31 is also provided with an air-bleed port 31b, and when the blood pressure measurement is completed the magnetic valve 31 opens to allow the air in the cuff 19 to bleed out through the air-bleed port 31b.

In addition to the pressure sensor (omitted from the drawings), the power switch 22, the measurement switch 23, the memory switch 24, and the initial pressurization value set switch 25 are positioned on an IC chip 43, together with a necessary wiring system for supplying power and signals to the pressurizing pump 26.

The liquid crystal display device 33, which displays the blood pressure values and the like, is connected to the circuit substrate 32 through a flat cable 38.

The battery housing chamber 34, which is integrally formed with the lower casing 18, houses a battery (omitted from the drawings).

Figure 6:
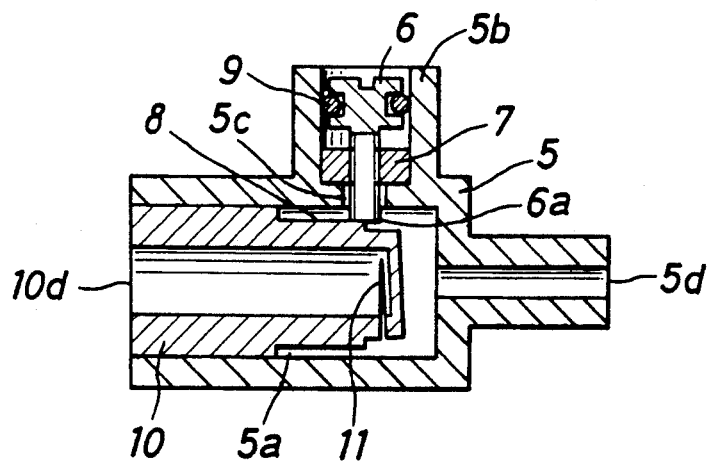
FIG. 6 is a sectional view of one embodiment of the constant rate air-bleed valve used with the electronic sphygmomanometer of the present invention.

FIG. 6 is a sectional view of one embodiment of the constant rate air-bleed valve used with the electronic sphygmomanometer of the present invention.

Figure 7:
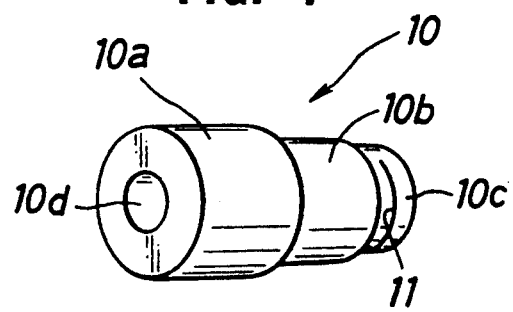
FIG. 7 is a perspective view of a tubular member incorporating the constant rate air-bleed valve shown in FIG. 6.

A tubular member 10 which is illustrated in FIG. 7 is positioned inside an air-bleed valve casing 5. One end of the tubular member 10 is open, and the other end is formed as an elastic member fabricated from rubber (such as, for example, silicone rubber or NBR, of a spring-type hardness of 60°) and is closed. The tubular member 10 comprises a large diameter section 10a, a medium diameter section 10b, and a small diameter section 10c, the diameters of all these sections being different. A fine slit 11 is formed in the radial direction in the small diameter section 10c of the tubular member 10, which is the same direction as the forward movement of a later-described adjusting member 6. The large diameter section 10a of the tubular member 10 is engaged by a medium diameter diameter section 5a of the air-bleed valve casing 5 while ensuring air tightness.

The air-bleed valve casing 5 is shaped as a hollow tube. A projection 5b for housing a regulating member 6 is provided on the surface of the cylinder. A nut 7 is embeddedly secured in the projection 5b, and the regulating member 6 can be screwed into the nut 7 causing the regulating member 6 to advance. A tip 6a of the regulating member 6 penetrates through a small hole 5c in the side surface of the air-bleed valve casing 5, and the tip 6a is formed so that it presses against an outer peripheral surface 8 of the tubular member 10. When the regulating member 6 is screwed into the nut 7, an opening is formed in the slit 11 proportional to the amount by which the regulating member 6 is screwed in. An O-ring 9 is provided on the head of the regulating member 6 to ensure the airtightness of the regulating member 6. In the air-bleed regulating device of this configuration, the air piping system of the sphygmomanometer has an open end 10a on the low pressure side and a pressure side port 5d on the high pressure side.

As shown in FIG. 4, the constant rate air-bleed valve is positioned in the lower casing 18 so that the longitudinal direction of the tubular member 10 becomes the lateral direction of the constant rate air-bleed valve, and the projection 5b, which is the regulating part, is positioned facing upward so that regulation from the top is possible.

The operation of the electronic sphygmomanometer of the present invention will now be explained.

To use the electronic sphygmomanometer, the cuff 19 is first wrapped around the upper arm of the patient whose blood pressure is to be measured and the power switch is turned ON.

Next, the initial pressurization value set switch 25 is pressed, and the initial pressurization value is optionally selected. In this embodiment of the present invention, the liquid crystal display device 33 shown in FIG. 3 is set for 160 mm Hg.

The pressurization pump 26 is then started by pressing the measurement switch 23. Specifically, the diaphragm 27 is activated vertically through the rotation of the shaft 30a of the motor 30 so that when the diaphragm 27 moves upward, the air intake valve 27b opens and air is drawn into the chamber 40 through the air intake port 28a, and when the diaphragm 27 moves downward, the air-bleed valve 27c opens and air is discharged from the chamber 40 through the air-bleed port 28b. By the repetition of these operations at high speed, air is supplied to the inside of the cuff 19. The pressure inside the cuff 19 is measured through a pressure sensor (omitted from the drawings) connected via the rubber tube 37. When the pressure reaches the initially set pressurization value of 160 mm Hg the rotation of the motor 30 is halted.

Next, the air in the cuff 19 passes through the rubber tubes 20, 36, the air-bleed port 28b of the pressurizing pump 26, and the channel 41, and, as shown in FIG. 6, is fed to the pressure side port 5d provided on the air-bleed pump casing 5 of the constant rate air-bleed valve. The air is then eliminated through the slit 11 in the tubular member 10. A normal air-bleed rate of 3 to 4 mm Hg/sec is desired.

At the same time, the air pressure in the cuff 19 is transmitted to the pressure sensor (omitted from the drawings) through the rubber tube 37 so that the air pressure and the body pulse are detected by the pressure sensor. The systolic and diastolic blood pressure values of the patient whose blood pressure is being measured are calculated and displayed on the liquid crystal display device 33.

When the measurement is completed, the magnetic valve 31 opens and the air in the cuff 19 is rapidly discharged from the air-bleed port 31b.

The measured blood pressure values can be recorded by pressing the memory switch 24.

Because the slit in the constant rate air-bleed valve of the electronic sphygmomanometer of the present invention is provided in the radial direction, it is possible to reduce the longitudinal dimension of the valve, making it possible to provide a constant rate air-bleed valve of reduced overall size. Furthermore, the rate of pressure drop required for the blood pressure measurement can easily be set by means of the regulating member, and once the rate of pressure drop is set, because of the configuration, when the air-bleed pressure is high, the slit is opened a small amount and the air-bleed rate is high, and when the air-bleed pressure is low, the slit is opened a large amount and the air-bleed rate is low. Therefore an almost constant rate can be maintained. Accordingly, the necessary 2 to 4 mm Hg/sec pressure drop rate for the blood pressure measurement from the systolic to the diastolic blood pressure can be easily obtained so that the blood pressure can be effectively and accurately measured.

In the embodiment as above described, the tubular member is positioned so that the longitudinal direction of the tubular member is the lateral direction of the constant rate air-bleed valve, and the regulating member can be operated on the upper side of the constant rate air-bleed valve. It is therefore possible for a user of the sphygmomanometer to control pressure from above, even if components such as a magnetic valve and circuit board are arranged in close proximity to one another.

What is claimed is:

1. An electronic sphygmomanometer comprising:
   a cuff;
   an electric pump adapted to be driven by a battery, said pump being coupled to said cuff for pressurizing the cuff;
   a pressure sensor coupled to said cuff for detecting a pulse and the air pressure inside said cuff;
   a constant rate air-bleed valve that is coupled to said cuff for reducing the pressure in the cuff at a constant rate, said constant rate air-bleed valve including:
      a tubular casing having first and second ends, said first end being coupled to said cuff and in fluid communication therewith, said second end being open to atmosphere;
      an elastic tubular member positioned in said casing, said tubular member having a closed end and an open end, said closed end being in the vicinity of the first end of said casing and said open end being open to atmosphere, said tubular member including a slit formed therein in the circumferential direction thereof, said slit being adjacent said closed end; and
      a regulating member having first and second portions, said regulating member being movably coupled to said casing such that said first portion can be pressed against the outer peripheral surface of said tubular member in the vicinity of said closed end, said second portion being exposed such that the position of the regulating member can be regulated from outside the air-bleed valve casing; and
   a display device coupled to said cuff for displaying the systolic and diastolic blood pressure values of a patient whose blood pressure is being measured, these values being calculated based on the air pressure and the pulse detected by said sensor.

2. The electronic sphygmomanometer according to claim 1 wherein said tubular member includes first and second sections, said first section having a smaller diameter than said second section, said slit being formed in said first section, said regulating member being oriented for contact with said second section.

3. The electronic sphygmomanometer according to claim 1 wherein said regulating member is threadingly coupled to said casing such that it can be screwed for advancement in the radial direction of said tubular member.

4. The electronic sphygmomanometer according to claim 1 wherein the air-bleed valve casing is integrally formed with a casing member which forms the electric pump.

5. The electronic sphygmomanometer according to claim 1 wherein said tubular and regulating members each have a longitudinal axis, said longitudinal axes being generally normal to one another, and the second portion of said regulating member being positioned facing upward so that regulation from above is possible.

6. An electronic sphygmomanometer according to claim 1 wherein the slit of the tubular member is formed in the same direction as the direction of advancement of the regulating member.

7. A sphygmomanometer comprising:
   a cuff configured to be arranged about a limb of a patient, said cuff forming an inflatable pressure chamber;
   a constant rate air-bleed valve that is coupled to said cuff for reducing the pressure in the cuff chamber at a constant rate, said constant rate air-bleed valve including:
      a tubular casing having first and second ends, said first end being coupled to said cuff and in fluid communication therewith, said second end being open to atmosphere;
      an elastic tubular member positioned in said casing, said tubular member having a closed end and an open end, said closed end being in the vicinity of the first end of said casing and said open end being open to atmosphere, said tubular member including a slit formed therein, said slit being adjacent said closed end and extending in the circumferential direction of said tubular member; and a regulating member having first and second portions, said regulating member being movably coupled to said casing such that said first portion can be pressed against the outer peripheral surface of said tubular member in the vicinity of said closed end, said second portion being exposed for adjusting the position of the regulating member.

* * * * *